United States Patent [19]

Wurzel

[11] Patent Number: 4,781,715

[45] Date of Patent: Nov. 1, 1988

[54] CARDIAC PROSTHESIS HAVING INTEGRAL BLOOD PRESSURE SENSOR

[75] Inventor: David Wurzel, Center Square, Pa.

[73] Assignee: Temple University of the Commonwealth System of Higher Education, Philadelphia, Pa.

[21] Appl. No.: 857,896

[22] Filed: Apr. 30, 1986

[51] Int. Cl.⁴ .............................................. A61F 2/22
[52] U.S. Cl. ....................................................... 623/3
[58] Field of Search ................... 623/3; 128/675, 672, 128/653, 748, 419

[56] References Cited

U.S. PATENT DOCUMENTS

| | | | |
|---|---|---|---|
| 3,358,690 | 12/1967 | Cohen | 128/419 PG |
| 3,718,044 | 2/1973 | Joyce, Jr. et al. | 73/223 |
| 3,974,825 | 8/1976 | Normann | 128/1 D |
| 4,162,543 | 7/1979 | Shumahov | 623/3 |
| 4,397,049 | 8/1983 | Robinson et al. | 623/3 |
| 4,465,063 | 8/1984 | Nielsen et al. | 128/1 D |

OTHER PUBLICATIONS

"Long Term In Vivo Automatic Electronic Control of the Artificial Heart", Landis et al, Trans. ASA 10, vol. 23, 1977.

Y. L. Sheng et al., "Indwelling Acoustic Sensor for Early Detection of Total Artificial Heart Failures", unpublished paper presented at International Biomedical Engineering Symposium and Exposition, Jan. 20-23, 1986, Salt Lake City, Utah.

Primary Examiner—Richard J. Apley
Assistant Examiner—James Prizant
Attorney, Agent, or Firm—Seidel, Gonda, Lavorgna & Monaco

[57] ABSTRACT

An integral blood pressure sensor for a cardiac prosthesis of the type having a fluid chamber and a blood chamber separated by a flexible diaphragm which is actuated by a drive fluid pulsatingly supplied to the fluid chamber for pumping blood from the blood chamber. The blood pressure sensor includes at least one transducer integral with a wall of the blood chamber and in pressure-sensing relation to the interior of the chamber. The invention also includes a method of manufacturing a cardiac prosthesis having an integral blood pressure sensor.

10 Claims, 1 Drawing Sheet

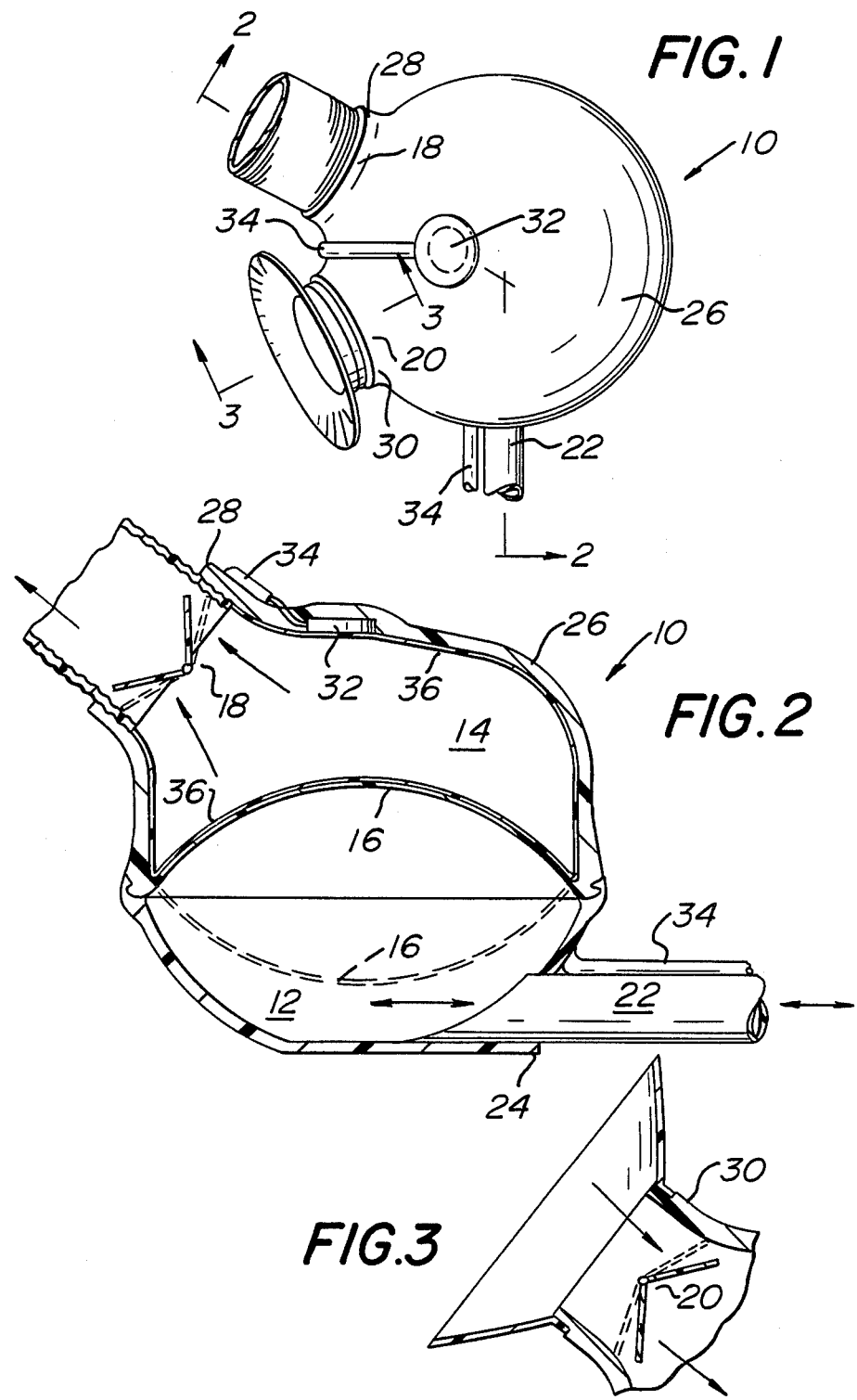

CARDIAC PROSTHESIS HAVING INTEGRAL BLOOD PRESSURE SENSOR

FIELD OF THE INVENTION

This invention relates to cardiac prostheses and, in particular, cardiac prostheses which are implantable in the human body for total cardiac replacement or cardiac assist applications.

BACKGROUND OF THE INVENTION

Cardiac prostheses for total cardiac replacement are, of course, known, and cases of total cardiac replacement using a cardiac prosthesis are attended by a great deal of publicity. Thanks to recent advances in technology and medical procedures, it is now possible to treat critically ill heart patients in some cases by total replacement of a defective heart with a cardiac prosthesis. The development and refinement of cardiac prosthesis has been the subject of intensive research in recent years, and great advances in this area are being made.

One of the more promising types of cardiac prosthesis which has been developed is a two-chamber device made of a semi-rigid urethane polymer. This device has a fluid chamber and a blood chamber separated by a flexible diaphragm. The blood chamber contains prosthetic heart valves to regulate the entry and exit of blood to and from the blood chamber. The pumping action of the prosthesis is controlled by a "heart driver" whose function is to impart a pumping action to the flexible diaphragm. This may be done mechanically, hydraulically or pneumatically. For example, in one type of pneumatic unit the heart driver is connected to the fluid chamber of the cardiac prosthesis by a flexible plastic tube connected to a source of compressed air. The heart driver controls the supply of air so as to alternately supply compressed air to the fluid chamber during systole (i.e., during the phase of the heart's operation where blood is pumped from the heart) and then to exhaust or draw air from the fluid chamber during diastole (i.e., that phase of the heart's operation where the heart is relaxed and the blood re-enters the heart chamber). During systole, the compressed air supplied to the fluid chamber exerts a force on the blood contained in the blood chamber via the flexible diaphragm. This force causes the flexible diaphragm to expel the blood from the blood chamber through the outflow valve. The duration of the systolic phase of operation is controlled by the heart driver. At the end of the systolic phase, the air is exhausted or drawn from the fluid chamber. This releases the pressure on the flexible diaphragm so that blood can refill the blood chamber via the inflow valve.

One lingering problem that has plagued the use of cardiac prostheses is the difficulty of obtaining reliable direct measurements of hemodynamic parameters such as blood pressure in the blood chamber. Although several methods have been employed to measure blood pressure, all of them have severe practical problems or risks associated with their use in that they invariably require some type of invasive technique.

For example, blood pressure may be measured using a catheter tipped transducer (e.g., the well-known Millar catheter) which must be inserted through the wall of the blood chamber through a special port built into the chamber wall to place the catheter. This port introduces a discontinuity in the flow of blood through the prosthesis and may eventually become a site of thrombogenesis, or clotting. In some cases a clot so formed can move through the patient's blood stream and lodge in the brain, causing a stroke. In addition, a typical Millar catheter can cost several thousand dollars, and is highly fragile and irreparable.

Because of the difficulty in using invasive techniques for measuring blood pressure, and the potential for thrombogenesis, these techniques are not practical for research or clinical cardiac prostheses use.

SUMMARY OF THE INVENTION

The present invention solves these problems by providing a non-invasive technique for measuring blood pressure in the blood chamber of a cardiac prosthesis. In a cardiac prosthesis having a fluid chamber and a blood chamber separated by a flexible diaphragm, the diaphragm being actuated by a drive fluid pulsatingly supplied to the fluid chamber for pumping blood from the blood chamber, the present invention provides means for sensing the pressure of the blood in the blood chamber comprising at least one transducer means integral with a wall of the blood chamber and in pressure-sensing relation to the interior of the chamber. The present invention also includes a method of manufacturing a cardiac prothesis having a transducer means integral with a wall of the blood chamber and comprises molding the transducer into a wall of the blood chamber when the blood chamber is molded.

DESCRIPTION OF THE DRAWINGS

For the purpose of illustrating the invention, there is shown in the drawings a form which is presently preferred; it being understood, however, that this invention is not limited to the precise arrangements and instrumentalities shown.

FIG. 1 is a top plan view of a cardiac prosthesis having an integral blood pressure transducer in accordance with the invention.

FIG. 2 is a sectional view of the cardiac prosthesis of FIG. 1, taken along lines 2—2 in FIG. 1.

FIG. 3 is a partial sectional view of the cardiac prosthesis of FIG. 1, taken along the lines 3—3 in FIG. 1.

DETAILED DESCRIPTION OF THE INVENTION

Referring now to the drawings, wherein like numerals indicate like elements, there is shown in FIGS. 1 and 2 a cardiac prosthesis 10 including an integral blood pressure transducer in accordance with the invention. The prosthesis 10 is separated into two chambers, a fluid chamber 12 and a blood chamber 14, by a flexible diaphragm 16. A pumping action may be imparted to the flexible diaphragm 16 by means of a drive fluid, such as compressed air, which alternately enters and is exhausted from fluid chamber 12, as represented by the double-headed arrow in FIG. 2.

For purposes of the invention, the cardiac prosthesis 10 may be any pneumatically-driven artificial heart or ventricular assist device, such as the much-publicized Jarvik 7 artificial heart. The cardiac prosthesis 10 is preferably made from a semi-rigid urethane polymer which can be formed by any suitable forming technique, preferably a vacuum-molding technique.

Flexible diaphragm 16 is impervious to gas or blood, but transmits pressure differences between the fluid and blood chambers by flexing and therby differentially varying the chamber volumes. For example, during systole the diaphragm is causdd to flex by compressed air so that it moves to the position such as illustrated by the solid lines in FIG. 2. In this configuration, the diaphragm exerts a force on the blood in blood chamber 14, expelling it through an outflow valve 18, as represented by the single-headed arrows in FIG. 2. During diastole, the pressurized gas is exhausted or drawn from fluid chamber 12. Blood then re-enters blood chamber 14 through an inflow valve 20, as represented by the single-headed arrows in FIG. 3, and displaces the diaphragm to a position such as that shown in phantom in FIG. 2.

Fluid chamber 12 is connected to a driver tube 22 which conducts the compressed air into and out of fluid chamber 12. Separate tubes and separate openings may be provided, if desired, for inlet and outlet of the compressed air. Typically, as shown in FIG. 2, fluid chamber 12 is fitted with a tubular port 24 for connection to driver tube 22.

The other end of driver tube 22 is connected to a heart driver (not shown) which may be electrically controlled by appropriate circuitry so that it alternately supplies compressed air during systole and exhausts the air during diastole.

Although it is not essential for understanding the present invention, a more complete understanding of the drive system of cardiac prosthesis 10 can be found in U.S. Pat. No. 4,465,063.

As seen in FIGS. 1 and 2, blood chamber 14 comprises a generally hemispherical wall 26, which, as noted above, can be formed by any suitable technique, preferably by vacuum molding. The manner in which blood chamber 14 can be formed is well-known, and need not be described in detail here. During formation of blood chamber 14, hemispherical wall 26 is provided with a blood outflow port 28 and a blood inflow port 30. Blood inflow port 30 and outflow port 28 are provided with suitable fittings so that the cardiac prosthesis may be connected by the surgeon to the atrial remnant and ascending aorta, respectively, of the patient.

During formation of blood chamber 14, a blood pressure transducer 32 is integrally formed into hemispherical wall 26. Although the exact placement of blood pressure transducer 32 in hemispherical wall 26 is believed not to be critical, it is preferably located on a portion of hemispherical wall 26 opposite flexible diaphragm 16. Connected to blood pressure transducer 32 are electrical conductors 34, which are brought out through the exterior of hemispherical wall 26 and are dressed around the outside of hemispherical wall 26 and run alongside driver tube 22. Thus, conductors 34 may be brought out through the patient's chest wall alongside driver tube 22 to the heart driver, which is located extrasomatically to the patient. Alternatively, transducer 32 may be provided only with terminals (not shown) to which suitable electrical leads may be connected after the cardiac prosthesis 10 is fabricated.

As best seen in FIG. 2, blood pressure sensor is in pressure-sensing relation to the interior of blood chamber 14 but does not protrude into the chamber. Instead, blood pressure transducer 32 is separated from the interior of blood chamber 14 by a continuous intima, or lining, 36 which lines the entire interior surface of blood chamber 14. Lining 36 is preferably a polyurethane lining, which can be formed by any suitable method, such as liquid casting. Lining 36 is made very thin relative to the thickness of hemispherical wall 26, so that the presure within blood chamber 14 is transmitted without a significant pressure drop to pressure transducer 32.

Lining 36 must be continuous and must have no seems so that there are no discontinuities in the path of blood flowing into and out of blood chamber 14. It is well-known that discontinuities in the path of blood flow can lead to thrombogenesis. By eliminating these discontinuities with a continuous, smooth lining 36, the risk of thrombogenesis in chamber 14 is minimized.

It will be appreciated that, since blood pressure sensor 32 is in pressure-sensing relation with the interior of blood chamber 14 without physically projecting into blood chamber 14, blood pressure within blood chamber 14 can be sensed non-invasively. The need for a catheter to be inserted into the interior of blood chamber 14, and thus the need for a special port for the catheter in hemispherical wall 26, are completely eliminated. Accordingly, the discontinuity which would be introduced by an invasive catheter, and the concomitant risk of thrombogenesis at the catheter site, are eliminated. The invention also eliminates the need for an additional opening in the patient's chest wall for insertion of the catheter. By eliminating the need for a second opening in the patient's chest wall, a potential site of infection is also eliminated.

Although blood pressure transducer 32 may be any suitable transducer, a preferred transducer is a silicon transverse voltage strain gage transducer. All silicon pressure transducers are piezoresistive devices, producing a change in output voltage when a sensing element's resistance changes due to physical deformation of the element under pressure. Current is passed through the transducer and, as pressure is applied to the transducer, an electric field is established and the resulting voltage sensed. The voltage provides an electrical signal representative of the pressure sensed by the transducer. A typical silicon transverse voltage strain gage transducer is the Motorola MPX Series pressure sensor.

The voltage output signal of pressure transducer 32 may be processed by suitable electronics and used to display blood pressure on a monitor, and may also be used as a feedback signal to control the pressure of compressed air supplied to fluid chamber 12. That is, blood pressure transducer 32 can provide a feedback siqnal to regulate the patient's blood pressure by controlling the heart driver.

It will be appreciated by those skilled iri that art that the present invention provides a dramatic improvement in blood pressure sensing in a cardiac prosthesis. With the present invention, blood pressure in the blood chamber of the prosthesis is sensed directly in a non-invasive manner with a minimum risk of thrombogenesis.

The present invention may be embodied in other specific forms without departing from the spirit or essential attributes thereof and, accordingly, reference should be made to the appended claims, rather than to the foregoing specification, as indicating the scope of the invention.

I claim:

1. A cardiac prosthesis having a fluid chamber and a blood chamber separated by a flexible diaphragm, the diaphragm being actuated by a drive fluid pulsatingly supplied to the fluid chamber for pumping blood from the blood chamber, means for noninvasively sensing the pressure of the blood in the blood chamber comprising at least one pressure transducer means located between the endocardial and epicardial surfaces of a wall of the blood chamber for substantially maintaining the characteristics of the endocardial surface of said wall blood and in pressure-sensing relation to the interior of the chamber.

2. In a cardiac prosthesis according to claim 1, wherein the transducer means comprises a piezoresistive device.

3. In a cardiac prosthesis according to claim 2, wherein the piezoresistive device comprises a silicon transverse voltage strain gage.

4. In a cardiac prosethesis according to claim 1, further comprising a continuous, smooth lining on the interior surface of the blood chamber, the lining being in pressure-transmitting relation to the transducer means and between the transducer means and the interior of the blood chamber.

5. In a cardiac prosthesis according to claim 1, wherein the transducer means is molded into the wall of the blood chamber during formation thereof.

6. In a cardiac prosthesis according to claim 1, further comprising electrical conductor means for connecting the output of the transducer means to signal processing means.

7. A cardiac prosthesis having a fluid chamber and a blood chamber separated by a flexible diaphragm, the diaphragm being actuated by a drive fluid pulsatingly supplied to the fluid chamber for pumping blood from the blood chamber, a noninvasive blood pressure transducer integrally formed into a wall of the blood chamber between the endocardial and epicardial surfaces thereof and in pressure-sensing relation to the interior of the chamber and a continuous, substantially smooth lining on the interior surface of the blood chamber in pressure-transmitting relation to the transducer and between the transducer and the interior of the blood chamber.

8. A method of making a cardiac prosthesis having a fluid chamber and a blood chamber separated by a flexible diaphragm and having a noninvasive blood pressure transducer in a wall of the blood chamber, comprising the steps of forming the transducer into a wall of the blood chamber between the endocardial and epicardial surfaces thereof when the wall is formed and forming a continuous, substantially smooth lining on the interior surface of the blood chamber whereby the transducer is in pressure-sensing relation to the interior of the blood chamber and separated therefrom by the continuous lining.

9. The method according to claim 8, wherein the step of forming the wall of the blood chamber comprises a vacuum molding process.

10. A method of noninvasively sensing blood pressure in the blood chamber of a cardiac prosthesis having a fluid chamber and a blood chamber separated by a flexible diaphragm actuated by a drive fluid pulsatingly supplied to the fluid chamber for pumping blood from the blood chamber, comprising integrally molding a blood pressure transducer into a wall of the blood chamber between the endocardial and epicardial surfaces of the wall during formation thereof, sensing the change of an electrical parameter of the transducer as a result of changes in blood pressure in the blood chamber, and electronically processing the change in the electrical parameter to derive an electronic signal representative of the blood pressure in the blood chamber.

* * * * *